(12) United States Patent
Kretz

(10) Patent No.: US 6,415,793 B1
(45) Date of Patent: Jul. 9, 2002

(54) DUAL DIRECTION VALVE SYSTEM

(76) Inventor: John Kretz, 9092 Jamison Rd., Lodi, OH (US) 44254

( * ) Notice: Subject to any disclaimer, the term of this patent is extended or adjusted under 35 U.S.C. 154(b) by 0 days.

(21) Appl. No.: 09/224,771

(22) Filed: Jan. 4, 1999

(51) Int. Cl.[7] ................................................ A62B 9/02
(52) U.S. Cl. .......................... 128/205.24; 128/206.15
(58) Field of Search ................... 128/206.15, 205.24; 137/493.2, 493.8

(56) References Cited

U.S. PATENT DOCUMENTS

| | | | |
|---|---|---|---|
| 1,885,121 A | * 11/1932 | Loweke | 137/493.2 |
| 2,133,575 A | * 10/1938 | Rosenberg | 137/493.2 |
| 2,431,457 A | 11/1947 | Bondurant | 277/45 |
| 3,470,904 A | * 10/1969 | Hune et al. | 137/493.2 |
| 3,580,273 A | * 5/1971 | Schwarz | 137/493.2 |
| 3,705,600 A | * 12/1972 | Heggen | 137/493.2 |
| 3,941,149 A | 3/1976 | Mittleman | 137/493.1 |
| 3,976,096 A | * 8/1976 | Kass et al. | 137/493.2 |
| 4,180,066 A | 12/1979 | Milliken et al. | 128/205.24 |
| 4,298,023 A | 11/1981 | McGinnis | 137/529 |
| 4,582,058 A | 4/1986 | Depel et al. | 128/207.17 |
| 4,823,828 A | 4/1989 | McGinnis | 137/102 |
| 4,854,574 A | 8/1989 | Larson et al. | 128/205.24 |
| 5,002,050 A | * 3/1991 | McGinnis | 128/205.24 |
| 5,004,008 A | * 4/1991 | Drucker | 137/493.2 |
| 5,301,667 A | 4/1994 | McGrail et al. | 128/205.14 |
| 5,385,140 A | * 1/1995 | Smith | 128/203.24 |
| 5,425,358 A | 6/1995 | McGrail et al. | 128/205.24 |

OTHER PUBLICATIONS

European Patent Office Search Report for EP Application No. EP 99120423; Jun. 28, 2001.

* cited by examiner

Primary Examiner—Aaron J. Lewis
(74) Attorney, Agent, or Firm—Cummings & Lockwood

(57) ABSTRACT

A dual direction exhalation valve is disclosed herein. The exhalation valve includes first and second sealing discs which are each movably mounted within a housing. The first sealing disc includes at least one venting aperture that is initially obstructed by the second sealing disc. In response to an appropriate pressure force, the second sealing disc flexes or deflects such that the at least one venting aperture is exposed. Upon removal of the motivating pressure, the second sealing disc automatically returns to its initial, obstructive position. A method for venting gas from an inhalation system is also disclosed which utilizes a dual direction exhalation valve.

10 Claims, 3 Drawing Sheets

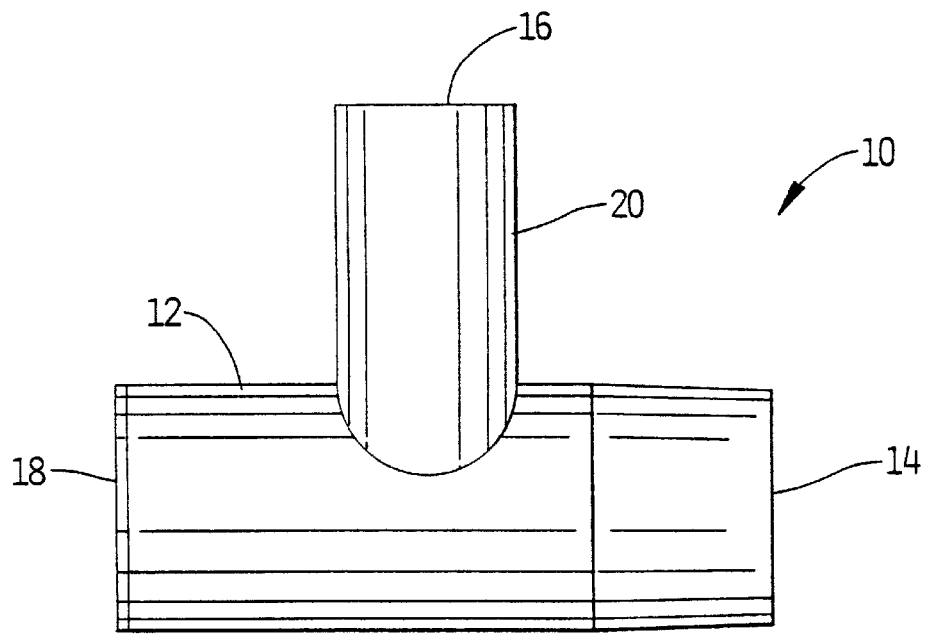
FIG_1
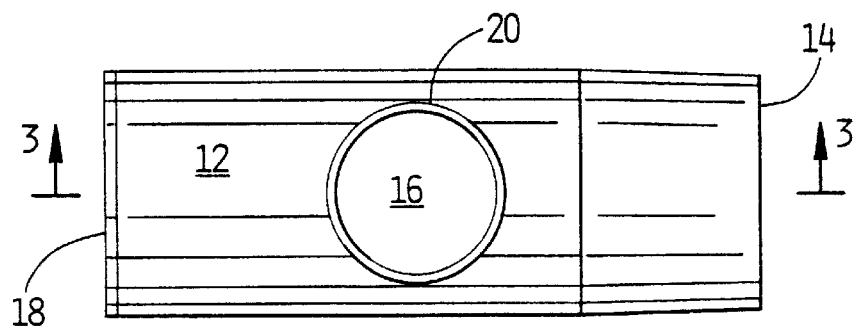
FIG_2

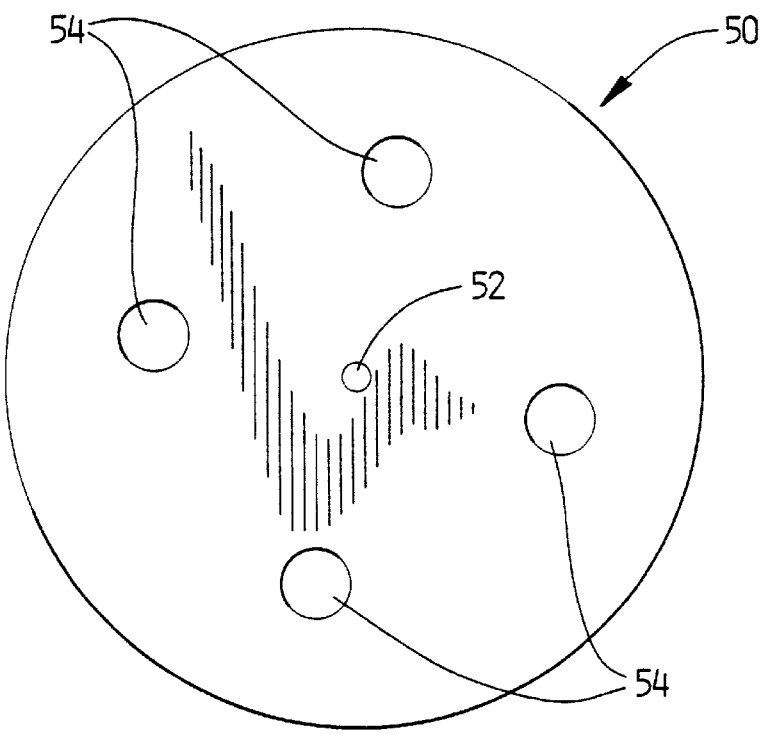
FIG_4
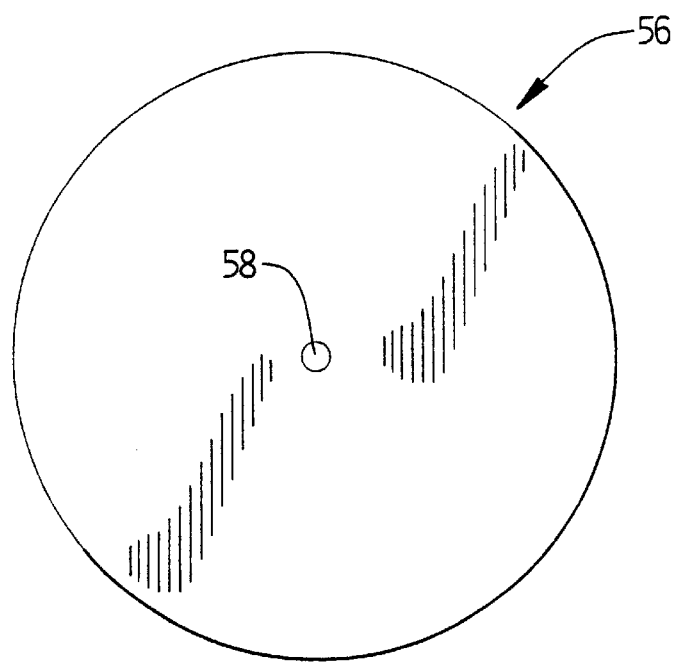
FIG_5

DUAL DIRECTION VALVE SYSTEM

BACKGROUND OF THE DISCLOSURE

1. Technical Field

The present disclosure relates to a unique valve system that is adapted to permit egress of gases and/or fluids in two directions. In particular, the present disclosure is directed to a valve system that is adapted to limit or regulate the peak inspiratory pressure of gases delivered to patients, while also limiting or regulating the peak pressure permitted downstream on the opposite side of such valve system.

2. Background Information

A variety of techniques and systems have been developed to assist physicians in treating or assisting patients with inhalation and/or ventilation issues. In many of these techniques, valving systems are desirable to ensure that the patient encounters or experiences the optimal pressure within the inhalation and/or ventilation system during the stages of inhalation and exhalation. Numerous relatively complicated pressure limiting valves, and pressure limiting systems, are known for controlling the peak inspiratory pressure of ventilation gas delivered to a patient, e.g, an infant, during manual ventilation.

Among known valve systems are reusable, adjustable metal pop-off valves which incorporate a spring and disc. These valve systems generally function to control the peak inspiratory pressure of ventilating gas once the preset threshold is attained. An issue with these pop-off valves is the possibility that the patient will be exposed to excess ventilation gas in the period when the pressure is building toward the preset threshold, a condition referred to as "Positive End Expiratory Pressure" or "PEEP." Illustrative valving systems are described in a series of U.S. Patents which are assigned to Vital Signs, Inc. (Totowa, N.J.). U.S. Pat. No. 4,180,066 to Milliken et al. describes an anesthesia gas scavenging system that includes a first negative pressure relief valve and a second valve which provides both positive and negative pressure relief. The second valve, which is illustrated in FIGS. 3 and 4, includes a pair of discs (32, 40) which are movable relative to each other and to the valve housing. Disc 32 is mounted to a spindle which translates through an aperture in disc 40 to permit venting through apertures 42 in response to a negative pressure within the gas scavenging system. Disc 40, in turn, is spring biased by coil spring 38 into sealing engagement with raised ridge 30, but is adapted to move against the bias of spring 38 in response to a sufficient positive pressure within the gas scavenging system. The Milliken '066 two disc valve system, which is highly tolerance-dependent, is particularly suited to a gas scavenging system and relies on a relatively complex set of motions to achieve its desired effects.

U.S. Pat. Nos. 5,301,667 and 5,425,358 to McGrail et al. disclose a pressure limiting valve for a ventilation gas apparatus which is adapted to independently vent in response to pressures above a peak inspiratory ventilation gas pressure and a base line pressure. In a disclosed embodiment, a spring is provided which biases a disc into engagement with a valve seat. The force delivered by the spring establishes or determines the peak inspiratory pressure, because a higher pressure within the gas ventilation apparatus is required to overcome the spring bias so as to vent the system. A disclosed embodiment further features a bleed hole or aperture which functions to establish and/or control the base pressure within the ventilation system.

A further exhalation valve for inhalation therapy is disclosed in U.S. Pat. No. 4,298,023 to McGinnis. The McGinnis '023 exhalation valve features a valve closure disc that is biased into engagement with a valve seat by a plurality of constant force compression springs. Through the use of the constant force compression springs, the McGinnis '023 exhalation valve advantageously maintains a desirable airway pressure within the inhalation system at a substantially constant pressure over a relatively wide range of flow rates. A commercial product incorporating, inter alia., the teachings of the McGinnis '023 patent has been successfully marketed by Vital Signs, Inc. (Totowa, N.J.) for several years.

Despite the careful attention that has been given the design of valving systems for use with inhalation and/or ventilation systems by those skilled in the field, a need for improvement remains. In particular, exhalation valves of the type disclosed in the aforementioned McGinnis '023 patent would benefit from features adapted to address exigencies that might be encountered during use.

SUMMARY OF THE PRESENT DISCLOSURE

According to the present disclosure, an exhalation valve is provided which advantageously functions to advantageously maintain a desirable airway pressure within an inhalation system at a substantially constant pressure over a relatively wide range of flow rates. The exhalation valve of the present disclosure also advantageously provides a further venting feature which obviates the potential for undesirable pressure build-ups within the inhalation system in the event certain exigencies are encountered during use of the exhalation valve. Further functions and advantages of the exhalation valve disclosed herein will be apparent from the detailed disclosure which follows.

In a preferred embodiment of the presently disclosed exhalation valve, a first sealing disc is spring-biased into sealing engagement with a valve seat. The first sealing disc is adapted to move out of engagement with the valve seat in response to a positive pressure within the inhalation system that exceeds a predetermined value. The predetermined value is established by the spring force applied to the first sealing disc. In a preferred embodiment, a plurality of constant force springs act on the first sealing disc to generate a relatively uniform resistance force.

In addition, a second sealing disc is preferably provided according to a preferred embodiment of the present disclosure. The second sealing disc is generally substantially coplanar with the first sealing disc, but of a lesser diameter (if the two discs are circular) or outermost dimension, as the case may be. The second sealing disc is generally resilient or flexible such that deflection of the disc along its surface is permitted. The second sealing disc is positioned in an adjacent, juxtaposed orientation relative to the first sealing disc, on the side of the first sealing disc opposite that against which the spring bias is applied.

Both first and second sealing discs generally include a first opening or aperture through which a mounting rod or nipple may pass. The first sealing disc also preferably includes at least one additional opening or aperture through which gas may be vented, as described herein. The second sealing disc is sized and dimensioned to overlie the at least one additional opening in an initial rest position, such that venting of gas therethrough is prevented. However, in response to an appropriate pressure force, the second sealing disc is adapted to flex or deflect such that the at least one additional opening is exposed and gas is free to pass therethrough. Once the appropriate pressure force is removed, the second sealing disc automatically returns to its initial non-flexed or non-deflected position, thereby preventing further flow of gases therethrough.

BRIEF DESCRIPTION OF THE DRAWINGS

The foregoing features of the exhalation valve of the present disclosure will become more readily apparent to and will be more fully understood by those of skill in the art by referring to the detailed description which follows with reference to the drawings, wherein:

FIG. 1 is a side view of an illustrative exhalation valve according to the present disclosure;

FIG. 2 is a top view of the illustrative exhalation valve of FIG. 1;

FIG. 4 is a top view of an illustrative first sealing disc according to the present disclosure; and FIG. 5 is a top view of an illustrative second sealing disc according to the present disclosure.

DETAILED DESCRIPTION OF PREFERRED EMBODIMENT(S)

Figure 3:
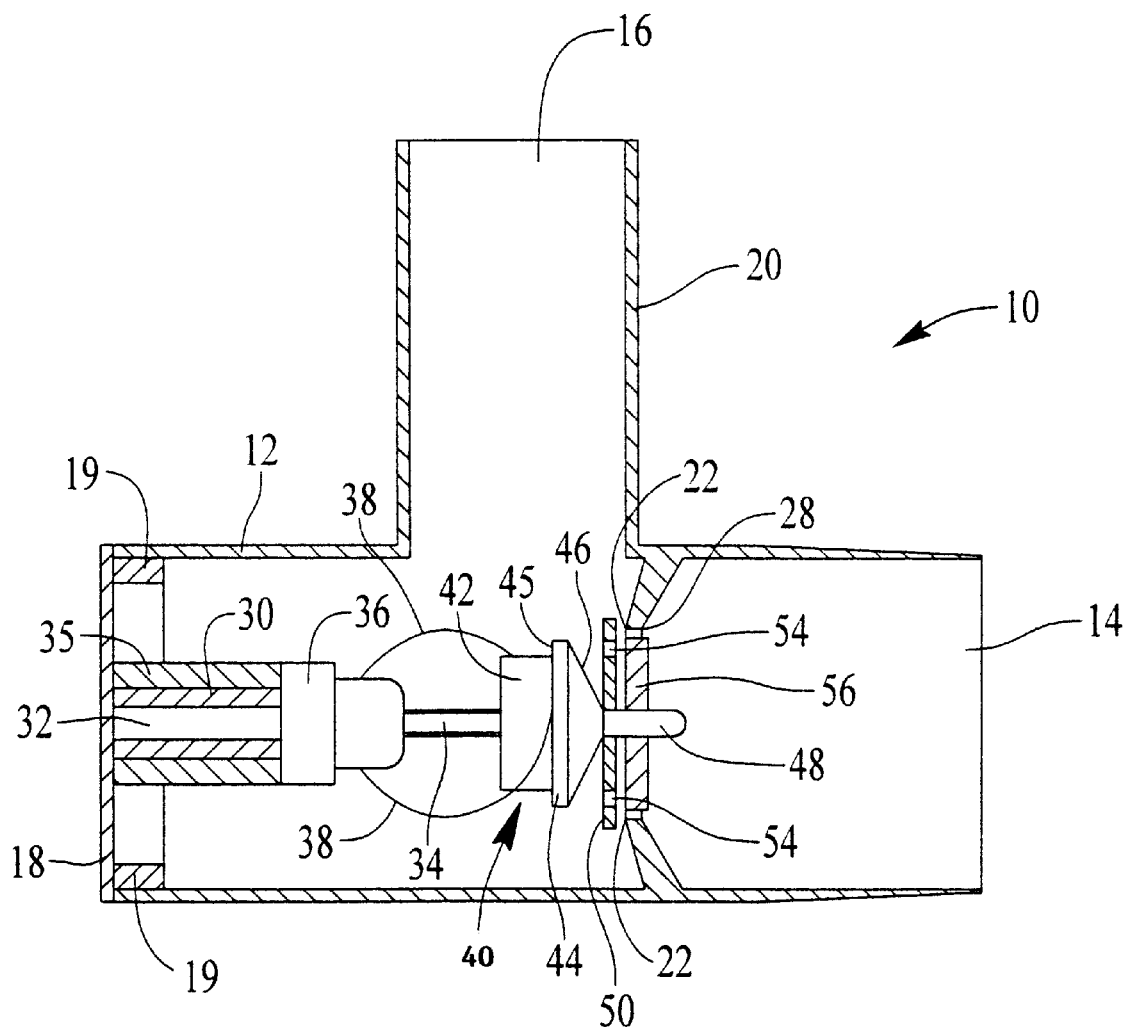
FIG. 3 is a cross-sectional view of the illustrative exhalation valve, taken along line 3—3 as shown in FIG. 2.

Referring initially to FIGS. 1 and 2, an exhalation valve 10 is disclosed which includes a tee-shaped housing 12 that defines a first flow opening 14 and a second flow opening 16. The third leg of the tee is sealed by wall 18. Flow openings 12 and 14 are circular in shape and the flow passages through housing 12 are substantially circular in cross-section. Housing 12 may be fabricated from any material suitable for medical applications, such as a suitable metal or plastic. In a preferred embodiment, housing 12 is molded from a polypropylene material and wall 18 is bonded to housing 12, e.g., by a suitable adhesive, sonic welding or the like.

Referring to the cross-sectional view of FIG. 3, the internal features of exhalation valve 10 are depicted. In the illustrated embodiment, wall 18 includes an inwardly extending circular flange 19 which is sized to closely approximate the circular opening in housing 12 to be obstructed by wall 18. Housing 12 forms a circular valve seat 22 which defines a substantially circular passage 28 that communicates with both openings 14 and 16. Thus, in the absence of some obstruction, gases and/or fluids would be free to pass from opening 14, through circular passage 28 which is defined within valve seat 22, and out of opening 16.

In addition to circular flange 19, a stem-receiving extension 30 is either molded as part of or joined to wall 18, and may be fabricated from a material of appropriate strength and rigidity, e.g., a polypropylene material of the type used in fabricating housing 12. Stem-receiving extension 30 extends substantially perpendicular to wall 18 and is preferably circular or square in cross-section. Stem-receiving extension 30 defines a space 32 within which a stem 34 may enjoy unencumbered travel, as described herein. Surrounding stem-receiving extension 30 is a spacer 35 and a spring mounting member 36 to which springs 38 are mounted. Spacer 35 and spring mounting member 36 may be fabricated from any medically suitable material, but spring mounting member 36 is preferably fabricated from a rubber material so as to facilitate, inter alia., formation and performance of spring mounting fingers (not pictured) onto which the springs 38 may be mounted. In a preferred embodiment, a plurality of constant force compression springs 38 of the type disclosed in U.S. Pat. No. 4,298,023 to McGinnis are utilized in the presently disclosed exhalation valve 10.

Indeed, preferred springs 38 and a preferred method for mounting springs 38 to spring mounting member 36 are disclosed in the aforementioned U.S. Pat. No. 4,298,023 to McGinnis, the entire disclosure of which is incorporated herein by reference.

As noted previously, one end of each spring 38 is mounted to or otherwise captured by spring mounting member 36. The other end of each spring 38 is mounted to or otherwise captured by disc mount 40. As with spring mounting member 36, disc mount 40 may be fabricated from any medically suitable material, but is preferably fabricated from a rubber material to facilitate interaction with springs 38. Disc mount 40 includes a flange-portion 42, a disc 44 having a flat first face 45 and a sloped second face 46, and a nipple 48 extending from the sloped second face 46. Stem 34 is mounted to flange portion 42 of disc mount 40 and extends therefrom into space 32 of stem-receiving extension 30. Space 32 is sized and configured to maintain alignment of stem 34 within housing 12 so as to ensure the functionality of the sealing discs described hereinbelow.

With reference to FIGS. 3 and 4, a first sealing disc 50 is mounted to disc mount 40 by passing nipple 48 through central aperture 52 formed in first sealing disc 50. The relative sizes of nipple 48 and central aperture 52 need not be tightly controlled because the retention of first sealing disc 50 on nipple 48 will be assured by the presence of other structure(s), as described herein. First sealing disc 50 is generally substantially flat and is preferably fabricated from a relatively rigid plastic, e.g., the same polypropylene used in fabricating housing 12.

In addition to central aperture 52, first sealing disc 50 includes at least one and, as disclosed in illustrated embodiment, four venting apertures 54. Venting apertures 54 may be uniform or varied in size and geometry, and may be uniformly or non-uniformly positioned around central aperture 52. In one preferred embodiment, four circular venting apertures 54 are uniformly positioned around central aperture 52, each having a diameter of from 0.15 to 0.2 inches. In this preferred embodiment, the diameter of first sealing disc 50 is approximately 0.76 inches and venting apertures which are opposite each other relative to central aperture 52 are spaced by 0.376 inches (aperture center to aperture center). Although the above-described specifics (e.g., geometries, dimensions and spatial relationships) represent a preferred embodiment, the present disclosure is in no way to be limited to the specifics of such disclosed embodiment.

Referring to FIGS. 3 and 5, a second sealing disc 56 is provided which includes a second central aperture 58. In a preferred embodiment, second central aperture 58 is sized and configured such that second sealing disc 56 frictionally engages nipple 48 when positioned thereon. Indeed, second sealing disc 56 is also positioned on nipple 48 and, in its initial position as depicted in FIG. 3, is positioned in an adjacent, juxtaposed orientation relative to first sealing disc 50. If sufficient friction exists between second central aperture 58 and nipple 48, no additional precaution need be taken to ensure that both first and second sealing discs 50, 56 retain their desired position with respect to nipple 48 and housing 12. However, if desired, a locknut, grommet or the like (not pictured) may be positioned on the exposed end of nipple 48 (after first and second sealing discs 50, 56 have been slid to their desired locations) to further strengthen the positioning of the sealing discs relative to nipple 48.

Second sealing disc 56 is sized and configured to overlie venting apertures 54 in its initial, at rest position, such that gases are prevented from flowing through venting apertures 54. Second sealing disc 56 is preferably fabricated from a resilient or flexible material, e.g., silicone, such that second sealing disc 56 is capable of flexing or deflecting away from first sealing disc 50 (in response to an appropriate pressure) to allow gas flow through venting aperture(s) 54. Thus, the point at which second sealing disc 56 will move sufficiently away from one or more venting apertures 54 and thereby permit gas flow therethrough is directly dependent upon the properties of second sealing disc 56 which influence is flexibility or deflection properties. These properties include the type(s) of material from which second sealing disc 56 is fabricated, its thickness (including whether its thickness is uniform or non-uniform proceeding from second central aperture 58), any coatings or other treatments which may be employed with respect to second sealing disc 56, and the like.

In the preferred embodiment described hereinabove with regard to the geometric and dimensional characteristics of first sealing disc 50, in such embodiment second sealing disc 56 preferably has a diameter of approximately 0.63 inches, a thickness of approximately 0.03 inches, and the diameter of second central aperture 58 is 0.09 inches.

It is contemplated that exhalation valves of the type disclosed herein may be fabricated to relieve pressures at various pressure levels, e.g., 2.5 cm $H_2O$, 5 cm $H_2O$, 7.5 cm $H_2O$, 10 cm $H_2O$, 20 cm $H_2O$, and the like. These variations are easily accommodated based on the teachings herein. For example, the performance of first sealing disc 50 may be varied by modifying the numbers and/or properties of springs 38; similarly, the performance of second sealing disc 56 may be varied by modifying the thickness, uniformity of thickness and/or materials used to fabricate second sealing disc 56. The ability to finely dial the desired properties of exhalation valve 10, based on the teachings of the present disclosure, should be readily apparent to persons of ordinary skill in the art.

Thus, as depicted in FIG. 3, a dual direction valve is provided within housing 12. If a sufficient positive pressure is introduced to housing 12 through flow opening 14 to overcome the spring force exerted on disc mount 40 by springs 38, then first sealing disc 50 will move out of sealing engagement with valve seat 22 to permit gas flow thereby. As first sealing disc 50 moves away from valve seat 22, stem 34 travels within opening 32 formed in stem-receiving extension 30. In addition, second sealing disc 56 travels in equal measure with first sealing disc 50 because both are mounted on nipple 48 which extends from disc mount 40. Upon sufficient venting or an independent reduction in the pressure being introduced to housing 12 through flow opening 14, springs 38 will restore first sealing disc 50 sealing engagement with valve seat 22.

Conversely, in response to a sufficient positive pressure being introduced to housing 12 through flow opening 16, second sealing disc 56 will flex or deflect away from first sealing disc 50, thereby exposing venting aperture(s) 54. Venting aperture(s) 54 will remain exposed, and gas will continue to flow therethrough, until such time as sufficient gas has vented or there is an independent reduction in the pressure being introduced to housing 12 through flow opening 16. At such time as the pressure is sufficiently reduced, second sealing disc 56 will automatically return to its initial non-flexed or non-deflected position and once again obstruct gas passage through venting aperture(s) 54.

The dual direction valve disclosed herein is advantageous in several respects. First, the present disclosure provides a valve system which ensures reliable valving performance, whether the "excess" pressure is encountered through flow opening 14 or flow opening 16. Second, the present disclosure provides a valve system that safeguards against unexpected and unregulated pressure build-up within an inhalation system in the event of an exigency, such as improper installation of an exhalation valve such that the intended input opening is oriented as an output passage. The dual direction valve of the present disclosure would ensure that the inhalation system would vent at predetermined pressures, regardless of the direction in which the valve experienced the pressure buildup.

Throughout the present disclosure, performance of the disclosed valve system has been described in connection with positive pressures and pressure build-ups. However, as will be readily apparent to persons of ordinary skill in the art, the presently disclosed valving system will function equally reliably in response to "negative" pressures (e.g., partial vacuum conditions). For example, in connection with the embodiment depicted in FIG. 3, if a sufficient negative pressure were introduced to housing 12 through flow opening 14, second sealing disc 56 would flex or deflect in a manner comparable to the flexure/deflection to be encountered in response to a sufficient positive pressure entering housing 12 through flow opening 16. Accordingly, throughout the present disclosure, the performance of exhalation valves manufactured in accordance with the present disclosure in response to negative pressures should be readily apparent.

Although the present disclosure has been described with reference to disclosed embodiments and with reference to certain aspects which are presently preferred, it will be understood by those skilled in the art that various modifications and changes in form and detail may be made without departing from the scope and spirit of the present disclosure, as claimed herein. For example, it may be desirable to include printed indicia on the exterior of housing 12 to communicate the preferred direction of fluid flow through exhalation valve 10 (e.g., arrows and associated verbiage). Other modifications and changes may no doubt be apparent to persons of skill in the art, upon a reading of the present disclosure. As noted herein, such modifications and changes will be understood not to depart from the scope and spirit of the present disclosure, as claimed herein.

What is claimed is:

1. A dual directional valve for regulating peak inspiratory and expiratory pressures of gases delivered to patients, comprising:

a housing fabricated from a material suitable for medical applications having a first leg portion, a second leg portion and a third leg portion, the first and second leg portions defining first and second flow openings respectively, the first and second flow openings defining a passage for gases;

a wall sealing the third leg portion to define a chamber within the housing, the chamber being substantially divided from the passage;

a valve seat disposed within the housing in communication with the first and second flow openings;

a first sealing disc movably mounted within the chamber of the third leg portion and defining an outer periphery larger than the valve seat, said first sealing disc defining at least one venting aperture;

a bias member coupled to the wall and the first sealing disc to sealingly engage the first sealing disc and positioned to overlie the valve seat in a rest position; and a second sealing disc sized and mounted to overlie the at least one venting aperture in a rest position, such that when sufficient pressure exists at the first flow opening the first sealing disc moves away from the valve seat to allow gases to exit the second flow opening and when sufficient pressure exists at the second flow opening the second sealing disc deflects away from the at least one venting aperture to allow gases to exit the first flow opening.

2. A dual directional valve as recited in claim 1, wherein gases flow to a patient by entering the first flow opening, traversing the passageway and exiting the second flow opening.

3. A dual directional valve according to claim 1, wherein said second sealing disc is fabricated from a resilient material and said second sealing disc moves at least in part through flexure or deflection.

4. An dual directional valve according to claim 1, wherein said second sealing disc is positioned in an adjacent, juxtaposed orientation relative to said first sealing disc when in said rest position.

5. A dual directional valve according to claim 1, further comprising a stem movably mounted within said housing, and wherein said stem moves within a housing extension that functions to maintain alignment of said stem relative to said housing.

6. A dual directional valve according to claim 5, wherein said first and second sealing discs are mounted directly or indirectly to said stem, and alignment of said first and second sealing discs relative to said housing is achieved as a result of said housing extension maintaining alignment of said stem relative to said housing.

7. A dual directional valve according to claim 1, wherein said first sealing disc includes a plurality of venting apertures.

8. A dual directional valve according to claim 7, wherein said first sealing disc is circular and defines a circumference, and wherein said plurality of venting apertures are equally sized and uniformly positioned around said circumference.

9. A dual directional valve according to claim 7, wherein said first sealing disc includes four venting apertures.

10. A dual directional valve according to claim 9, wherein said four venting apertures are each circular and each has a diameter of approximately 0.15 inches.

* * * * *